United States Patent [19]

Olsson et al.

[11] Patent Number: 4,526,188
[45] Date of Patent: Jul. 2, 1985

[54] PROCESS AND APPARATUS FOR MIXING GASES IN A SPECIFIC PROPORTION AND DOSING THE RESULTANT GAS MIXTURE

[75] Inventors: Sven-Gunnar Olsson, Soedra Sandby; Björn Jonson, Lund; Hanna Neuman, Solna, all of Sweden

[73] Assignee: Siemens Aktiengesellschaft, Berlin & Munich, Fed. Rep. of Germany

[21] Appl. No.: 377,464

[22] Filed: May 12, 1982

[30] Foreign Application Priority Data

May 14, 1981 [SE] Sweden .................. 8103025

[51] Int. Cl.³ .................................... G05D 11/13
[52] U.S. Cl. ........................... 137/3; 137/88; 137/624.2
[58] Field of Search ........... 137/624.18, 624.2, 624.13, 137/624.15, 3, 88, 607

[56] References Cited

U.S. PATENT DOCUMENTS

| | | | |
|---|---|---|---|
| 3,219,046 | 11/1965 | Waugh | 137/487.5 X |
| 3,298,383 | 1/1967 | Cooper | 137/3 |
| 3,504,686 | 4/1970 | Cooper | 137/3 |
| 3,841,344 | 10/1974 | Slack | 137/7 X |
| 4,004,884 | 1/1977 | Zdrodowski | 137/624.8 X |
| 4,019,523 | 4/1977 | Clark | 137/624.2 X |
| 4,062,373 | 12/1977 | Clark | 137/3 |
| 4,162,689 | 7/1979 | Zdrodowski | 137/88 X |
| 4,262,686 | 4/1981 | Heim | 137/88 X |
| 4,345,610 | 8/1982 | Herter | 137/624.2 X |
| 4,392,514 | 7/1983 | Farley | 137/607 X |

OTHER PUBLICATIONS

N. V. Philips; Chemical Blending Plant Control Using 50-Series Modules; Applicant Note 31; pp. 1-6.

Primary Examiner—Alan Cohan
Attorney, Agent, or Firm—Hill, Van Santen, Steadman & Simpson

[57] ABSTRACT

A method of mixing a plurality of gases in a specified proportion and dosing the resultant gas mixture comprises supplying individually controlled gas streams from suitable sources thereof in a pulse-like fashion to an enclosed chamber from where the resultant gas mixture can be delivered to a point of use, such as a patient undergoing anesthesiological or respirational treatment. Each gas source is connected, via feed lines each having a back-pressure valve and an on-off solenoid valve, via a common flow line to an enclosed mixing chamber. A first and, optionally, a second flow meter are operationally positioned between the common flow line and the enclosed mixing chamber and generate electrical signals in accordance with select properties of the gas streams passing through such flow meter. These signals are transmitted to a microprocessor-controlled regulating unit, which also controls the solenoid valves in accordance with a specified program to provide desired gas pulses to the enclosed mixing chamber. A display means, a memory means and an alarm means can be operationally connected with the regulating unit.

3 Claims, 2 Drawing Figures

PROCESS AND APPARATUS FOR MIXING GASES IN A SPECIFIC PROPORTION AND DOSING THE RESULTANT GAS MIXTURE

BACKGROUND OF THE INVENTION

1. Field of the Invention

The invention relates to a process and apparatus for mixing gases in a specified proportion and dosing the resultant gas mixture to a point of use and somewhat more particularly the invention relates to a method and apparatus for precisely mixing various gases and transmitting known amounts thereof for anesthesiological and respirational treatments.

2. Prior Art

A known method of mixing gases for anesthesiological and/or respirational treatments utilizes mechanical systems which contain differential pressure regulators and throttle/valve arrangements. Such mechanical systems do not allow any greater precision than about ±3% and function only in a limited gas pressure flow range. Further, the function of such a system is unreliable in instances of low gas pressure. In order to obtain a satisfactory precision where small mixed gas streams are required, in certain instances, a larger gas stream must be transmitted through a mixer whereby a large portion of the provided gas quantity cannot be utilized. Yet further, a mechanical system of this type is not reliable because its function can be interfered with by dirt or the like reaching operational elements of the system. Through a functional interference of this type, the gas sources which are connected with such a mechanical system, can come into direct communication with one another so that gas can flow from one gas source with a higher pressure into another gas source with a lower pressure, particularly if the gas mixture is not removed from the mixing system. The results can entail catastrophic consequences; for example, when laughing gas ($N_2O$) and oxygen gas, which are both odorless, are being mixed, they can mistakenly be readily interchanged. Further, the dosing of the resultant gas mixture must be conducted with a specific apparatus that is not a component part of the mixing system; for example, with a rotary meter having an adjustable throttle or choking valve positioned after the mixing system.

Another known method of mixing and dosing gases comprises directly mixing a plurality of gases with the aid of individual rotary meters for each gas with series-connected adjustable throttles. In practice, with this type of an arrangement, precision of no more than about ±10% can be obtained. In order to obtain a gas mixture having a desired proportion of individual gases therein, the necessary flow for each gas must be precalculated and individually adjusted.

In anesthesia a desirable requirement is being able to record the concentration of the various gases in a gas mixture being utilized and being able to record the flow of this gas mixture. Further, another desirable requirement is for an alarm means which indicates when the composition of a gas mixture or when the volume of the gas stream does not agree with an adjusted (predetermined) value. These requirements cannot be satisfied with the systems that are based on the two above discussed methods; on the contrary, such requirements can only be satisfied by providing expensive electronic measuring devices.

SUMMARY OF THE INVENTION

The invention provides a precise, safe and reliable method and apparatus for mixing and dosing gases while simultaneously avoiding the earlier discussed prior art disadvantages.

In accordance with the principles of the invention, a plurality of individual gases are transmitted, via separate flow lines having controllable valve means, successively in a pulse-like fashion to a common flow line. The pulse gas quantities behave, in relation to one another, like the desired proportions between such gases in a mixture. Accordingly, the flow of the individual gas pulses is determined in one and the same flow meter means operationally coupled with the common flow line and the gas quantity in the individual gas pulses is controlled by regulating the length of such pulses in dependence on measured values obtained from the flow meter.

In certain embodiments of the invention, the flow of each gas pulse is determined by two flow meters which respond differently to specific properties of the gases and any deviation from a predetermined difference in such measurements results can be displayed and/or utilized to initiate operative counter-measures.

In certain embodiments of the invention, the individual gas pulses are supplied in the form of successive pulse trains wherein the gas quantities of the various gases in each pulse train are controlled in accordance with the proportion between such gases in the mixture. A time interval is provided between each pusle train and this interval is regulatable. The time interval between pulse trains can be regulated in such a manner that a specifiable average flow of the gas mixture results.

In certain embodiments of the invention, the flow meter means utilized to measure the gas flow can be reset to zero during the time interval between pulse trains.

In certain embodiments of the invention, the supply of pulse trains to the common flow line is determinable in dependence upon the quantity and/or pressure of gas mixture present in such common flow line.

By following the principles of the invention, one can randomly mix a plurality of various gases with maintained precision, safety and reliability.

Further, by following the principles of the invention, one can, in a simple fashion, sense whether a desired or correct gas is being supplied. Simultaneously, the invention allows one to record the mixing and dosing history during a given operation. This can be important for anesthesia in order to make clear, in retrospect, whether any errors were made or whether a functional error caused an erroneous proportioning or dosing of the gases. Further, the invention allows arranging alarm and/or blocking circuits for displaying erroneous functions and in instances of a significant functional error, to initiate appropriate operative counter-measures, such as altering feed rates or disconnecting relevant gas supply lines, etc.

DESCRIPTION OF THE PREFERRED EMBODIMENTS

Figure 1:
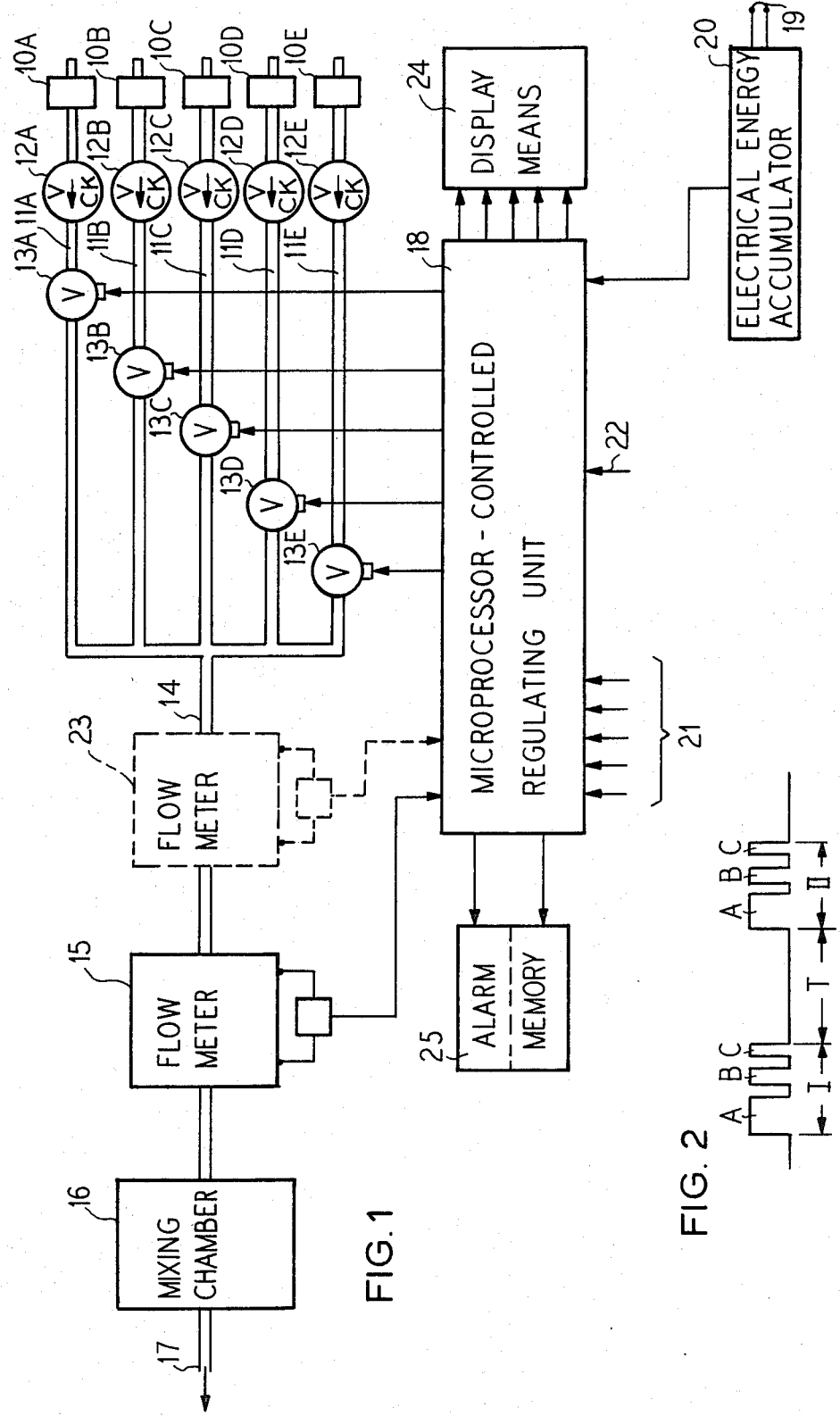
FIG. 1 is a schematic diagram of an anesthesia unit operable in accordance with the principles of the invention.

Referring now to FIG. 1, a number of gas connecting terminals 10A, 10B, 10C, 10D and 10E are provided for interconnection to suitable gas sources (not shown) and are interconnected to individual gas feed lines 11A, 11B, 11C, 11D and 11E. Each of the gas connecting terminals can be operationally coupled to various different pressurized gas sources for supplying different gases to the various gas feed lines. Such gas sources can contain, for example, air under relatively high pressure, air under relatively low pressure, pure oxygen ($O_2$), laughing gas ($N_2O$), oxygen saturated with Halothane ($C_2HBrClF_3$) or Etran ($CHF_2OCF_2CHClF$), etc.

Each gas feed line 11A through 11E is provided with a respective back-pressure valve means 12A, 12B, 12C, 12D and 12E and a solenoid valve means 13A, 13B, 13C, 13D, and 13E. After the respective solenoid valve means, the individual gas feed lines 11A through 11E are connected to a common flow line 14, which, via a flow meter means 15 is connected with an enclosed mixing chamber 16. The chamber 16 is provided with a dosing feed line 17 which is in fluid communication with a point of use, for example, such as a rubber bladder or some other means for supplying the mixed gas to a patient. The flow meter 15 can be of a type (for example, pneumotachographic) in which a gas stream flows through a series of parallel channels and the pressure drop over such channels is measured and converted with a differential manometer into an appropriate electrical signal. The mixing chamber 16, which can either be a separate unit or comprise a portion of a lung respirator, can be of the type which contains a bellows or the like biased by a spring arrangement (further details of which are set forth in Swedish Patent No. 358,296, which is incoprorated herein by reference).

Figure 2:
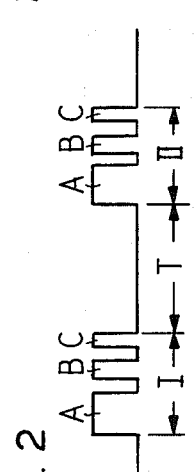
FIG. 2 is a diagrammatical illustration of a partial gas pulse train emitted by the anesthesia unit of FIG. 1.

The solenoid valves 13A through 13E are electrically connected to a microprocessor-controlled regulating unit 18 which operates via a mains current supply 220/110 volts, 50/60 Hz whereby the current supply is provided at electrical terminal 19 to an energy accumulator aggregate (multi-unit storage battery or the like) 20 for energizing the regulating unit 18 for a selected time period; for example, four hours, in the event the current from the electrical mains should be interrupted. Suitable microprocessors are known in the art. The regulating unit 18, which can be constructed according to known principles and whose detailed construction, given the current state of electronic technology, need not be described in greater detail herein, is provided for opening and closing the solenoid valves 13A through 13E in accordance with a specific program in order to allow the various gas pulses to pass through, from the respective gas sources connected at gas connecting terminals 10A through 10E via individual gas feed lines 11A through 11E and further through the common flow line 1114 via the flow meter means 15 to the enclosed mixing chamber 16, where the individual gas pulses are mixed for further controlled transportation of the resultant gas mixture through dosing line 17 to a point of use, for example a patient. In this manner, gas pulses are thus emitted in successive pulse trains, as schematically illustrated at FIG. 2, where two pulse trains I and II are separated from one another by a time interval T. Each pulse train illustrated at FIG. 2 is comprised of three separate pulses, which can relate, for example, to pulse A from the gas source connected to gas connection terminal 10A, a pulse C from the gas source connected to gas connection terminal 10C and a pulse D from the gas source connected to gas connection 10D. The individual gas volumes in each of the exemplary three gas pulses A, C and D behave in relation to one another like desired proportions of the individual gases from the respective gas sources in a desired gas mixture which is to be provided to a patient through gas dosing line 17. The mixing proportion of such gas mixture can therefore be altered as desired by selectively changing the gas volume in the respective gas pulses in a given gas pulse train. To this end, the regulating unit 18 is therefore provided with individual control means, schematically illustrated by arrows 21, for adjusting the gas volume in the individual gas pulses and, naturally, also for determining which gas sources are to emit or provide gas pulses to the particular gas pulse train. The total flow of the resultant gas mixture through the dosing line 17 is regulated by adjusting the time interval T between the various pulse trains. Therefore, the regulating unit 18 is also provided with another control means, schematically indicated by arrow 22, for adjusting the gas flow in this manner.

The flow meter 15 generates and transmits a signal to the regulating unit 18 and this flow signal functions as a feedback signal for regulating the volume in each gas pulse. Each gas pulse, in turn, is initiated by virtue of the fact that a revelant control means (valve) 21 is opened in accordance with an input program in the microprocessor-regulated unit 18, and each gas pulse is shut-off or terminated when the signal from the flow meter 15 indicates that a desired volume has passed through the flow meter.

Each individual gas pulse, independently of which gas source it originates from, is thus transmitted through one and the same flow meter and proportioned in dependence on the measurement results obtained from this flow meter, which delivers an appropriate signal to the regulating unit. Therefore, inaccuracies or defectiveness in the flow meter do not alter the mixing proportion of a desired gas mixture.

An additional advantage of regulating gas with a pulsating gas flow in accordance with the principles of the invention comprises in that the flow meter unit 15, during the time interval T between the respective gas pulse trains, i.e., when the gas flow is zero, can be reset to zero. As a consequence of the foregoing, the influence of a possible zero point drift in the flow meter can be avoided. With each measuring operation, after a gas of a known nature (chemical make-up) and character (physical property) has passed through the flow meter 15, it is easy for an operator to adjust the signal or signals generated by the flow meter to, for example, the different properties of the various respective gases, such as two gases having different viscosities or temperatures, or pressures, in the microprocessor of the regulating unit. Thus, by proceeding in accordance with the principles of the invention, the mixing proportion of gases can be very precisely adjusted.

The total volume of each pulse train is thus determined by the flow meter 15 with a correct proportion of the respective gases in the overall gas mixture. Further, in dependence on this gas pulse train volume, the time interval T between various pulse trains can also be determined so that a selected total gas flow of the gas mixture results. Because the flow meter can be reset to zero during the interval between gas pulse trains, the total flow of gas mixture can also be determined with great precision.

The initiation of a pulse train to the mixing chamber 16 can be commenced and/or terminated in accordance with the volume and/or pressure of the gas mixture present in the mixing chamber so as to keep the volume of the pressure automatically within specified parameters, independently of the quantity of gas mixture removed from the mixing chamber.

The gas connecting terminals 10A through 10E can be identified (i.e., marked and provided with specialized fittings) in accordance with international standards so that only gas sources containing a gas of the specified nature can be connected to each individual terminal. Nevertheless, serious accidents have occurred because gas from one gas source has flown to another gas source, as discussed earlier, or because a gas source (such as a pressurized tank) was delivered or filled with an incorrect gas content. In order to eliminate potential errors of this type, optionally, an additional flow meter 23, in addition to flow meter 15, can be provided in operational relation with the common feed line 14 and with the regulating unit 18. Flow meter 23 can be so selected that it responds differently to specific properties of the gas mixture flowing through line 14, than the flow meter 15. An exemplary embodiment of a flow meter of this type is described in *Acta Anaesth. Scand*, Volume 23 (1979), pages 349–358 (which is incorporated herein by reference). By comparison of the measurement result (for example, made by the microprocessor or the regulating unit 18) from flow meters 15 and 23, it can be determined whether in a given instance a correct gas is passing through the common flow line 14 because, for a given gas, the measurement results from the two flow meters 15 and 23 exhibit a predetermined difference. Therefore, a deviation from such predetermined difference can, by appropriate circuits, trigger a blocking or shut-off of the anesthesia unit or can trigger an appropriate alarm.

A signal display means, schematically indicated by box 24 can be operationally connected to the regulating unit 18 for the purpose of displaying the flow of the gas mixture as well as the concentration of the various different gases in the gas mixture. In addition, as schematically indicated by the two-unit box 25, a memory means and an alarm means can be coupled with the regulating unit 18 for recording the mixing-dosing progression and for controlling the regulating unit 18 in accordance with a stored program in the microprocessor and/or triggering an alarm if critical deviations from provided parameters should occur.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

We claim as our invention:

1. In a method of mixing a plurality of gases in a specified proportion and dosing the resultant gas mixture to a point of use whereby individual gases are transmitted via separate lines having controllable valve means successive in pulse-like fashion to a common line and the pulse gas quanitites of the various gases behave in relation to one another like the desired proportions between such gases in the mixture, wherein the improvement comprises:
   determining the flow of individual gas pulses in one and the same flow meter;
   controlling the gas quanitites of the individual gas pulses by regulating the length of such gas pulses in dependence on measured values obtained from said flow meter,
   said flow of individual gas pulses being determined by two flow meters which respond differently to specific properties of the gases and any deviation from a predetermined difference in such measurement results is displayed and/or utilized to initiate operative countermeasures.

2. An apparatus for mixing a plurality of gases in a specified proportion and dosing the resultant gas mixture to a point of use, comprising:
   a plurality of gas connecting terminals for connection to select gas sources;
   individual feed lines connected to each gas connecting terminal for transmitting the gas from each individual gas source to a common gas flow line;
   individual, successively positioned, back-pressure valve means and solenoid valve means in each gas feed line for regulating the flow of gas in such feed line;
   a flow meter means operationally connected with said common gas flow line for measuring the flow of gases therethrough and generating a corresponding electrical signal;
   an enclosed mixing chamber coupled with said common gas flow line for mixing the individual gas pulses with one another and dosing the resultant gas mixture to a point of use;
   a microprocessor-controlled regulating means electrically connected with said flow meter means and said solenoid valve means for controlling said solenoid valve means in accordance with programmed responses to said signal so as to provide desired gas pulses to said enclosed mixing chamber; and
   said flow meter means comprising two separate flow meters, each operationally connected with said common gas flow lines, each said flow meter responding differently to specific properties of gases flowing therethrough and generating an appropriate signal to said microprocessor-controlled regulating unit.

3. A method for mixing a plurality of different gases comprising the steps of,
   (A) successively and sequentially delivering into a common line each one of the gases of said plurality pulse-wise, such delivering of each such gas being carried out through a separate feed line, each separate feed line being provided with a fast acting controllable valve,
   (B) regulating the quantity of gas in each individual such pulse for each one of the gases of said plurality so that such individual pulse corresponds to the quantity of that gas in a desired gas mixture,
   (C) measuring the quantity of gas in each individual such pulse by a first flowmeter means located in said common line, and converting such measurements into a first signal output representative thereof,
   (D) correlating the quantity of gas conveyed in each individual such pulse with the length of such pulse, and determining a duration for each individual such pulse which corresponds to said quantity, and inputing such duration for each such pulse into a control means as a set point therefor, (E) delivering said first signal output from said first flowmeter means to said control means, and delivering a second signal output from said control means to each respective one of said valves in a successive and sequential manner, said second signal output being adapted to control each respective one of said valves, (F) programming said control means to operate respective ones of said valves responsively to successive and sequential first signal outputs from said first flowmeter means whereby a gas pulse of each one of said gases results through its associated valve which pulse corresponds to the quantity of each one of the gases of said pulrality in said desired gas mixture, (G) charging all gas in said common line into a mixing chamber means, (H) transporting gas from said mixing chamber means through a dosing line to a point of use, (I) a second flowmeter being located in a succession in said common line relative to said first flowmeter, and said second flowmeter reacting differently to different gas properties relative to said first flowmeter, and the quantity of gas in each individual such pulse being measured by said second flowmeter and such measurements being converted into a second signal output representative thereof, (J) a different respective measured value for the quantity of gas in ech individual such pulse being obtained from each of said first and said second flowmeters and thus a characteristic difference between these measured values is obtained for each gas of said plurality delivered pulse-wise into said common line, (K) said characteristic difference being stored in said control means as a comaprative value for comparison to each individual pulse of each gas of said plurality, and (L) if a deviation occurs for a given gas between a measured value difference and such stored value difference, then such deviation being indicated as an error.

* * * * *